United States Patent [19]

Surbey et al.

[11] 4,176,081

[45] Nov. 27, 1979

[54] SOLUTIONS OF ACRYLAMIDOALKANESULFONIC ACID SALTS IN ORGANIC LIQUIDS AND METHOD FOR THEIR PREPARATION

[75] Inventors: Donald L. Surbey, Lyndhurst; Alan C. Clark, Mentor; Leonard E. Miller, Chagrin Falls, all of Ohio

[73] Assignee: The Lubrizol Corporation, Wickliffe, Ohio

[21] Appl. No.: 877,940

[22] Filed: Feb. 15, 1978

Related U.S. Application Data

[63] Continuation-in-part of Ser. No. 816,117, Jul. 15, 1977, abandoned.

[51] Int. Cl.$^2$ .................. C07C 143/14; C08F 220/46; C08K 5/42
[52] U.S. Cl. ............................... 252/182; 260/513 N
[58] Field of Search ................... 260/513 N; 252/182

[56] References Cited

U.S. PATENT DOCUMENTS 2,983,712   5/1961   Wilkinson ................... 260/513 N X Primary Examiner—Benjamin R. Padgett
Assistant Examiner—Irwin Gluck
Attorney, Agent, or Firm—James W. Adams, Jr.; William H. Pittman

[57] ABSTRACT

Solutions of salts, especially sodium salts, of acrylamidoalkanesulfonic acids in organic liquids such as dimethylformamide are prepared by reacting the acid with a metal salt of a weak acid (preferably a metal carbonate or bicarbonate), or a cation exchange resin in the metal salt form, in the organic liquid in the presence of a free radical polymerization inhibitor (preferably an oxygen-containing gas such as air with which the mixture is blown) until the neutralization number of the mixture to phenolphthalein is a base number or, if an acid number, is no higher than about 1.0. In a preferred embodiment of the process, the mixture is blown with air and such blowing is continued until the acid number of the system is no greater than about 1.0, after which a strongly alkaline reagent is added until the neutralization number is a base number or an acid number no higher than about 0.1.

20 Claims, No Drawings

SOLUTIONS OF ACRYLAMIDOALKANESULFONIC ACID SALTS IN ORGANIC LIQUIDS AND METHOD FOR THEIR PREPARATION

This application is a continuation-in-part of copending application Ser. No. 816,117, filed July 15, 1977, now abandoned.

This invention relates to a method for processing salts of acrylamidoalkanesulfonic acids, and particularly for preparing stable, substantially water-free solutions of such salts in polar organic liquids. In its most general sense, the method of this invention comprises reacting said acrylamidoalkanesulfonic acid in said liquid with at least a stoichiometric amount of a metal base comprising at least one metal salt of a weak acid or cation exchange resin in the metal salt form in the presence of an inhibitor of free radical polymerization and at a temperature below the temperature of polymerization, said reaction being continued until the neutralization number of the solution to phenolphthalein is a base number or, if an acid number, is no higher than about 1.0.

Acrylamidoalkanesulfonic acids and their salts have been known for some time. Disclosures thereof can be found, for example, in U.S. Pat. No. 3,544,597 and British Pat. No. 1,341,104. The acids and their salts are useful monomers, particularly for copolymerization to form polymers having a wide variety of uses. Especially useful copolymers may be obtained by copolymerizing the acrylamidoalkanesulfonic acid or its salt with acrylonitrile, the product of which can be used for the production of dyeable acrylic fibers.

Many commercial methods for the preparation of acrylic fibers involve polymerization in polar organic solvents. It is frequently found that the copolymerization reaction is best effected when the salt of the acrylamidoalkanesulfonic acid, rather than the free acid, is used as the comonomer. However, these salts tend to undergo polymerization upon storage and it may therefore be advantageous to prepare the salt from the free acid just before use. In particular, it is often advantageous to prepare such salt in solution in the solvent to be used for polymerization.

A principal object of the present invention, therefore, is to prepare solutions in organic solvents of salts of acrylamidoalkanesulfonic acids.

A further object is to produce acrylamidoalkanesulfonate salt solutions which are substantially dry, highly storage stable, and capable of utilization as such in copolymerization reactions.

Other objects will in part be obvious and will in part appear hereinafter.

The acrylamidoalkanesulfonic acids useful in the method of this invention are well known in the art, and reference is made to the patents mentioned hereinabove as well as to other well known patents. Illustrative suitable acids may be represented by the formula

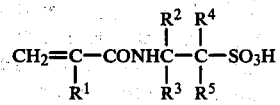

wherein $R^1$ is hydrogen or methyl and each of $R^2$, $R^3$, $R^4$ and $R^5$ is individually hydrogen or a lower alkyl radical, the word "lower" denoting radicals containing up to 7 carbon atoms. Examples of lower alkyl radicals are methyl, ethyl, n-propyl, isopropyl, 1-butyl, 2-butyl, 2-pentyl, 3-hexyl and 3-methyl-pentyl. The preferred acids are those in which $R^4$ and $R^5$ are each hydrogen, $R^2$ is a lower alkyl radical and $R^3$ is hydrogen or a lower alkyl radical, usually the latter. Illustrative acids are 2-acrylamidoethanesulfonic acid, 2-acrylamidopropanesulfonic acid, 2-methacrylamidopropanesulfonic acid, 2-acrylamido-2-methylpropanesulfonic acid, and 2-methacrylamido-2-methylbutanesulfonic acid. A particular preference is expressed for 2-acrylamido-2-methylpropanesulfonic acid, and to a somewhat lesser extent for its methacrylamido homolog.

The salts whose solutions may be prepared by the method of this invention include, in general, any metal salts which are soluble in the polar organic solvents used. These include in particular the alkali metal and alkaline earth metal salts, chiefly those of lithium, sodium, potassium, magnesium, calcium and barium, and especially those of sodium, potassium, magnesium and calcium. The method of this invention is particularly useful for the preparation of alkali metal and especially sodium salts.

The polar organic liquid may be any liquid suitable for the preparation of a solution of an acrylamidoalkanesulfonic acid salt. Preferred are liquids in which polymerization of the salt, especially copolymerization with such monomers as acrylonitrile, takes place with facility. Examples of useful polar organic solvents are alcohols such as methanol, ethanol and the propanols, and aprotic liquids including amides such as dimethylformamide and dimethylacetamide and sulfoxides such as dimethyl sulfoxide. The aprotic amides are preferred, notably N,N-dialkylamides such as the aforementioned dimethylformamide and dimethylacetamide. Of these, dimethylformamide is most preferred because of its availability and high degree of usefulness as a polymerization solvent.

The reaction which is crucial to the method of this invention is a simple neutralization of the acrylamidoalkanesulfonic acid, usually with a metal base comprising at least one metal salt of a weak acid such as carbonic, boric or acetic acid. The salt is most often a metal carbonate or bicarbonate, such as sodium carbonate or sodium bicarbonate. Also useful, in place of such salts, are cation exchange resins in the metal salt form (usually alkali metal and especially sodium), typically strong acid or weak acid resins in which the acid groups may be, for example, sulfonic or carboxylic acid groups.

In the preferred embodiments of the invention wherein the metal salt is a carbonate or bicarbonate, the products of the neutralization reaction are the salt of the acrylamidoalkanesulfonic acid, water and carbon dioxide. The amount of water and carbon dioxide produced when a bicarbonate is used is 1 mole of each per mole of salt obtained, while a carbonate produces only ½ mole of each per mole of salt obtained. Since it is preferable to minimize the amount of water and carbon dioxide present in the salt solution, the use of metal carbonates is especially preferred.

At least a stoichiometric amount of the metal base is used; that is, at least one equivalent thereof per equivalent of acrylamidoalkanesulfonic acid. It is preferred to use a slight excess of the metal base, typically about 1.1–1.25 equivalents per equivalent of acrylamidoalkanesulfonic acid.

The temperature at which the neutralization reaction is effected may be any temperature below that at which, under the conditions of the method of this invention, polymerization of the acrylamidoalkanesulfonic acid or its salt will take place. The system is rather highly susceptible to autopolymerization under conditions of relatively high acidity, so it is preferred to keep the reaction temperature fairly low (e.g., not above about 35° C. and preferably no higher than about 30° C.) at least until sufficient base has been introduced to render the reaction mixture nearly neutral, and preferably neutral or basic. The temperature may be allowed to increase as the basicity of the mixture increases, but it is usually neither necessary nor desirable for the temperature to exceed about 40° C.

The neutralization reaction is carried out in the presence of an inhibitor of free radical polymerization. Many suitable inhibitors are known; examples are hydroquinone monomethyl ether and hindered phenols such as t-butylcatechol and 2,6-di-t-butyl-p-cresol. Oxygen is a preferred inhibitor, and in a preferred embodiment of the invention an oxygen-containing gas is passed through the solution during the neutralization reaction. Suitable gases include oxygen and mixtures of oxygen with such relatively inert gases as nitrogen, helium and argon. An especially preferred oxygen-containing gas is air. While the invention is not limited by any theory of reaction, it is believed that the passage of oxygen accomplishes at least two things: It inhibits polymerization, and it drives evolved carbon dioxide from the solution so as to increase its basicity. Because the use of a bicarbonate as the metal base produces twice as much carbon dioxide (in molar terms) as the use of the corresponding carbonate, passage of an oxygen-containing gas is necessary for a lesser time when a carbonate is used than when the corresponding bicarbonate is used.

The order of addition of the acrylamidoalkanesulfonic acid and metal base to the organic liquid is not critical. However, to improve the stability of the system it is usually preferred to keep it basic for as long as possible. Thus, it is usually found advantageous to first dissolve or suspend the metal base in the liquid and subsequently to add the acrylamidoalkanesulfonic acid thereto. Acid addition may be gradual but gradual addition is not necessary, and it is often preferred to merely introduce the acid relatively rapidly in a single increment.

When the polymerization inhibitor is an oxygen-containing gas, its passage through the system is continued for some time after the acid and base have been introduced, so as to drive substantially all carbon dioxide therefrom and increase the stability of the acrylamidoalkanesulfonic acid salt solution. Gas passage may be discontinued when the solution contains free oxygen and is basic enough to be stable under normal storage conditions.

Basicity may be measured by a number of methods which will be apparent to those skilled in the art. For instance, pH meter readings may be taken and compared with those of comparable solutions of known stability. It is preferred, however, that the neutralization number of the solution be used as a criterion for cessation of gas passage. Several acid-base indicators are useful in neutralization number determinations and the neutralization number at which gas passage is stopped will vary with the indicator used. Phenolphthalein and bromphenol blue are commonly used and these two, especially the former, are preferred for the purposes of this invention. As used herein, "neutralization number" is either an "acid number" or a "base number" which are defined as the number of milligrams of potassium hydroxide (KOH) or of acid expressed in terms of the equivalent number of milligrams of potassium hydroxide, respectively, necessary to titrate to the appropriate end point a 10-gram sample of the solution being tested. The solutions in organic solvents contemplated according to the present invention should be diluted with a great excess of water before titration is effected to minimize any effect of the organic liquid on the indicator; typically, a 10-gram portion of the solution is diluted with distilled water to 100 ml. and this solution is titrated to determine the neutralization number.

During the method of this invention, the neutralization number is initially a relatively high acid number and becomes progressively lower during gas passage, often passing the neutral point as measured by phenolphthalein or bromphenol blue and becoming a base number which becomes progressively higher as gas passage continues. The solution is basic enough to be adequately stable for most purposes at an acid number of about 1.0 to phenolphthalein and a corresponding acid number of about 0.6 to bromphenol blue. It is stable enough for virtually all purposes at an acid number of about 0.1 to phenolphthalein and a corresponding base number of about 0.3 to bromphenol blue.

As previously noted, the resistance of the acrylamidoalkanesulfonic acid salt to autopolymerization increases as the basicity of the solution increases. In an especially preferred embodiment of the method of this invention, the acrylamidoalkanesulfonic acid and the metal base are initially introduced into the organic liquid, typically in a ratio of equivalents of base to acid of about 1.0–1.1:1, and passage of the oxygen-containing gas is effected as described hereinabove to an acid number to phenolphthalein no higher than about 1.0 (or to bromphenol blue no higher than about 0.6). A small amount of a strongly alkaline reagent is then added and passage of the gas is continued to a solution acid number to phenolphthalein no higher than about 0.1, or base number to bromphenol blue of at least about 0.3. The strongly alkaline reagent may be, for example, an alkali metal carbonate or bicarbonate or it may be sodium hydroxide, potassium hydroxide, an alkylamine such as triethylamine, or the like. When the salt used for neutralization is a metal carbonate or bicarbonate, it is usually convenient to use as the alkaline reagent the same salt (e.g., sodium carbonate). The amount of strongly alkaline reagent required in this step is usually no more than about 0.10–0.15 equivalent per equivalent of acrylamidoalkanesulfonic acid originally introduced.

As an alternative to addition of a strongly alkaline reagent, the solution may be contacted in this step with a cation exchange resin in the metal salt form. The resins and salts preferably used are the same as described hereinabove with reference to the initial neutralization step.

The acrylamidoalkanesulfonic acid salt solutions obtained by the method of this invention are, as previously noted, singularly stable under storage conditions and useful for polymerization, particularly copolymerization with such monomers as acrylonitrile. Because of their novelty and high degree of utility, the solutions themselves as well as the previously described method constitute an aspect of the invention.

The method of this invention is illustrated by the following examples. All parts and percentages are by weight.

EXAMPLE 1

A mixture of 4627 parts of dimethylformamide and 208 parts (3.92 equivalents) of anhydrous sodium carbonate is stirred and blown with air. 2-Acrylamido-2-methylpropanesulfonic acid, 738 parts (3.57 equivalents), is added over 20 minutes as stirring and air blowing are continued. The temperature of the mixture is maintained below 30° C. as the acid is added. Air blowing and stirring are continued for about 8½ hours, at the end of which time the acid number of the solution to phenolphthalein, after filtration, is 0.1. The solution is filtered using a filter aid; the filtrate is the desired 15% solution of sodium 2-acrylamido-2-methylpropanesulfonate in dimethylformamide.

EXAMPLE 2

A mixture of 38.15 parts (0.72 equivalent) of anhydrous sodium carbonate and 850 parts of dimethylformamide is stirred and blown with air as in Example 1, and 135 parts (0.65 equivalent) 2-acrylamido-2-methylpropanesulfonic acid is added. Air blowing is continued until the acid number of the solution to phenolphthalein is 0.93. Air blowing and stirring are continued as an additional 3.5 parts (0.066 equivalent, for a total of 0.79 equivalent) of sodium carbonate is added, and for an additional period until the acid number of the solution to phenolphthalein is 0.1. Upon filtration, the desired 15% solution in dimethylformamide is obtained.

EXAMPLE 3

The procedure of Example 2 is repeated except that potassium carbonate is substituted for the sodium carbonate, on an equal equivalent basis. The product is a solution of potassium 2-acrylamido-2-methylpropanesulfonate in dimethylformamide.

EXAMPLE 4

The procedure of Example 1 is repeated using dimethylacetamide rather than dimethylformamide as the solvent. A similar product is obtained.

EXAMPLE 5

The procedure of Example 1 is repeated using dimethyl sulfoxide rather than dimethylformamide as the solvent. A similar product is obtained.

What is claimed is:

1. A method for preparing a solution in a polar organic liquid of a metal salt of at least one acrylamidoalkanesulfonic acid which comprises reacting said acrylamidoalkanesulfonic acid in said liquid with at least a stoichiometric amount of at least one metal base selected from the group consisting of metal salts of weak acids and cation exchange resins in the metal salt form in the presence of an inhibitor of free radical polymerization and at a temperature below the temperature of polymerization, said reaction being continued until the neutralization number of the solution to phenolphthalein is a base number or, if an acid number, is no higher than about 1.0.

2. A method according to claim 1 wherein the metal base is an alkali metal or alkaline earth metal salt of a weak acid and the final neutralization number, if an acid number, is no higher than about 0.1.

3. A method according to claim 1 wherein the metal base is a carbonate.

4. A method according to claim 1 wherein the polymerization inhibitor is an oxygen-containing gas which is passed through the liquid until the desired neutralization number has been attained.

5. A method according to claim 4 wherein the metal base is an alkali metal or alkaline earth metal salt of a weak acid and the final neutralization number, if an acid number, is no higher than about 0.1.

6. A method according to claim 5 wherein the metal base is a carbonate.

7. A method for preparing a solution in a polar organic liquid of a metal salt of at least one acrylamidoalkanesulfonic acid which comprises passing an oxygen-containing gas through said liquid while reacting said acrylamidoalkanesulfonic acid therein with at least a stoichiometric amount of at least one metal base selected from the group consisting of metal carbonates and metal bicarbonates at a temperature below the temperature of polymerization; continuing passage of said gas through the system until the neutralization number thereof to phenolphthalein is an acid number no higher than about 1.0; and then adding a strongly alkaline reagent or a cation exchange resin in the metal salt form and continuing passage of said gas until the neutralization number is a base number or, if an acid number, is no higher than about 0.1.

8. A method according to claim 7 wherein the metal is an alkali metal or an alkaline earth metal.

9. A method according to claim 8 wherein the metal base and the strongly alkaline reagent are each the metal carbonate.

10. A method according to any of claims 1–9 wherein the organic liquid is an aprotic liquid.

11. A method according to claim 10 wherein the acrylamidoalkanesulfonic acid has the formula

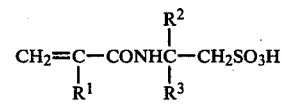

wherein $R^1$ is hydrogen or methyl, $R^2$ is lower alkyl and $R^3$ is hydrogen or lower alkyl.

12. A method according to claim 11 wherein the metal is an alkali metal.

13. A method according to claim 12 wherein the metal is sodium and the acrylamidoalkanesulfonic acid is 2-acrylamido-2-methylpropanesulfonic acid.

14. A method according to claim 13 wherein the organic liquid is at least one of dimethylformamide and dimethylacetamide.

15. A method according to claim 14 wherein the organic liquid is dimethylformamide.

16. A method according to claim 14 wherein the organic liquid is dimethylacetamide.

17. A storage stable solution prepared by the method of claim 11.

18. A storage stable solution prepared by the method of claim 12.

19. A storage stable solution prepared by the method of claim 13.

20. A storage stable solution prepared by the method of claim 15.

* * * * *